US008871148B2

(12) United States Patent
Wendland et al.

(10) Patent No.: US 8,871,148 B2
(45) Date of Patent: *Oct. 28, 2014

(54) MULTILAYER COLORIMETRIC SENSORS (75) Inventors: Michael S. Wendland, North St. Paul, MN (US); Neal A. Rakow, Woodbury, MN (US)

(73) Assignee: 3M Innovative Properties Company, St. Paul ( * ) Notice: Subject to any disclaimer, the term of this patent is extended or adjusted under 35 U.S.C. 154(b) by 203 days.

This patent is subject to a terminal disclaimer.

(21) Appl. No.: 13/320,925

(22) PCT Filed: May 19, 2010

(86) PCT No.: PCT/US2010/035378
§ 371 (c)(1),
(2), (4) Date: Nov. 17, 2011

(87) PCT Pub. No.: WO2010/135413
PCT Pub. Date: Nov. 25, 2010

(65) Prior Publication Data
US 2012/0062892 A1    Mar. 15, 2012

Related U.S. Application Data (60) Provisional application No. 61/180,483, filed on May 22, 2009.

(51) Int. Cl.
*G01N 21/00* (2006.01)
*G01J 1/48* (2006.01)
*G01J 3/46* (2006.01)
*B05D 5/06* (2006.01)
*G01N 21/77* (2006.01)
*G01N 21/78* (2006.01)

(52) U.S. Cl.
CPC ............. *G01N 21/77* (2013.01); *G01N 21/78* (2013.01); *G01N 21/783* (2013.01); *G01N 2021/7723* (2013.01); *G01N 2021/7773* (2013.01)
USPC ............ 422/82.11; 356/405; 422/82.05; 422/86

(58) Field of Classification Search
CPC .................................................. G01N 21/783
See application file for complete search history.

(56) References Cited

U.S. PATENT DOCUMENTS 4,641,524 A    2/1987    Tarvin
5,122,451 A    6/1992    Tanaka
(Continued)

FOREIGN PATENT DOCUMENTS

CN    1685225    10/2005
CN    1957246    5/2007
(Continued)

OTHER PUBLICATIONS

U.S. Appl. No. 13/320,948, entitled *Multilayer Colorimetric Sensor Arrays*, filed May 19, 2010.

*Primary Examiner* — Jill Warden
*Assistant Examiner* — Julie Tavares
(74) *Attorney, Agent, or Firm* — Kenneth B. Wood (57) ABSTRACT Herein are disclosed methods and devices for detecting the presence of an analyte. Such methods and devices may comprise at least one sensing element that comprises at least one optically responsive layer that comprises at least a highly analyte-responsive sublayer and a minimally analyte-responsive sublayer. Methods of making and using such sensing elements are also disclosed.

25 Claims, 3 Drawing Sheets

(56) References Cited

U.S. PATENT DOCUMENTS

| | | | |
|---|---|---|---|
| 5,611,998 A * | 3/1997 | Aussenegg et al. | 422/82.05 |
| 5,783,836 A | 7/1998 | Liu | |
| 6,007,904 A | 12/1999 | Schwotzer | |
| 6,130,748 A | 10/2000 | Kruger | |
| 7,368,294 B2 | 5/2008 | Nikitin | |
| 7,449,146 B2 | 11/2008 | Rakow | |
| 2004/0062682 A1 | 4/2004 | Rakow | |
| 2004/0184948 A1* | 9/2004 | Rakow et al. | 422/1 |
| 2007/0140907 A1 | 6/2007 | Rakow | |
| 2007/0141580 A1* | 6/2007 | David et al. | 435/6 |
| 2007/0297944 A1 | 12/2007 | Wendland | |
| 2008/0063575 A1 | 3/2008 | Rakow | |
| 2008/0063874 A1* | 3/2008 | Rakow et al. | 428/426 |
| 2009/0209420 A1 | 8/2009 | Kalgutkar | |
| 2011/0254568 A1 | 10/2011 | Thomas | |
| 2011/0257038 A1 | 10/2011 | Thomas | |
| 2011/0257281 A1 | 10/2011 | Thomas | |

FOREIGN PATENT DOCUMENTS

| | | |
|---|---|---|
| CN | 101326053 | 12/2008 |
| DE | 3424355 | 1/1985 |
| RU | 2 181 487 | 4/2002 |
| WO | WO 2005/111588 | 11/2005 |

* cited by examiner

MULTILAYER COLORIMETRIC SENSORS

CROSS REFERENCE TO RELATED APPLICATIONS

This application is a national stage filing under 35 U.S.C. 371 of PCT/US2010/035378, filed May 19, 2010, which claims priority to U.S. Provisional Application No. 61/180,483, filed May 22, 2009, the disclosure of which is incorporated by reference in its/their entirety herein.

BACKGROUND

The ability to detect chemical analytes, for example organic chemical analytes, is important in many applications, including environmental monitoring and the like. Such detection and/or monitoring of analytes may find particular use in, for example, personal monitors (e.g., that can be worn or carried by a person), and/or area monitors (e.g., that can be placed in a desired environment).

Many methods for the detection of chemical analytes have been developed, for example optical, gravimetric, microelectromechanical, and colorimetric. Though colorimetric devices currently exist for a range of analytes, most are based upon employing dyes or colored chemical indicators for detection. Such compounds are typically selective, meaning that multiple sensors may be necessary in order to detect various classes of compounds. Moreover, many of these systems have lifetime limitation issues, due to photo-bleaching or undesirable side reactions. Many such systems also rely on complicated or bulky optoelectronic components to carry out the optical interrogation.

SUMMARY OF THE INVENTION

Herein are disclosed methods and devices for detecting the presence of an analyte. Such methods and devices may comprise at least one sensing element that comprises at least one optically responsive layer that comprises at least a highly analyte-responsive sublayer and a minimally analyte-responsive sublayer.

Thus in one aspect, disclosed herein is an optically interrogatable sensing element for sensing an analyte, comprising an optically responsive layer between a reflective layer and a semi-reflective layer, wherein the optically responsive layer comprises at least a first, highly analyte-responsive sublayer and a second, minimally analyte-responsive sublayer.

Thus in another aspect, disclosed herein is a method of making a sensing element for sensing an analyte, comprising: forming a semireflective layer on an optically clear substrate; forming a layer of minimally analyte-responsive material atop the semireflective layer; forming a layer of highly analyte-responsive material atop the layer of minimally analyte-responsive material; and, forming an analyte-permeable reflective layer atop the layer of highly analyte-responsive material.

Thus in still another aspect, disclosed herein is a method of using a sensing element, comprising: providing an optically interrogatable sensing element for sensing an analyte, comprising an optically responsive layer between a reflective layer and a semi-reflective layer, wherein the optically responsive layer comprises at least a first, highly analyte-responsive sublayer and a second, minimally analyte-responsive sublayer; and, exposing the sensing element to an atmosphere potentially containing an analyte of interest.

These and other aspects of the invention will be apparent from the detailed description below. In no event, however, should the above summaries be construed as limitations on the claimed subject matter, which subject matter is defined solely by the attached claims, as may be amended during prosecution.

Like reference symbols in the various figures indicate like elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", bottom", "upper", lower", "under", "over", "front", "back", "outward", "inward", "up" and "down", and "first" and "second" may be used in this disclosure, it should be understood that those terms are used in their relative sense only unless otherwise noted. In particular, the characterization of certain parameters (e.g., concentration) in a given context as being "lower", "intermediate" and/or "higher" should be understood to be interpreted in a relative (comparative) sense within the given context (e.g., an "intermediate" concentration is between a "lower" and a "higher" concentration referred to in the same context).

DETAILED DESCRIPTION

Figure 1:
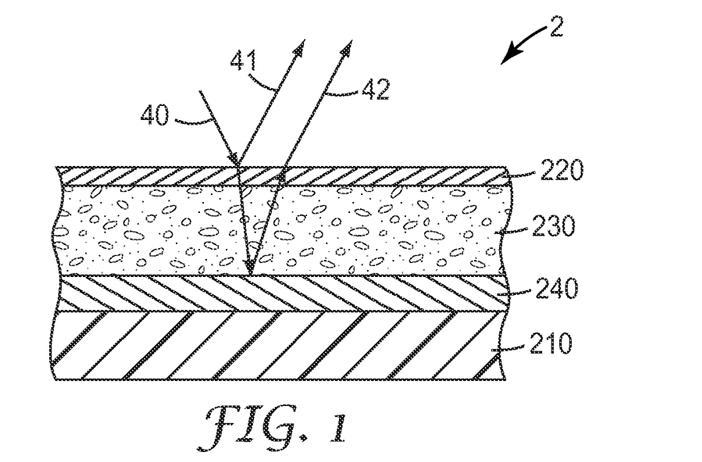
FIG. 1 is a side cross sectional view of a portion of an exemplary sensing element.
Figure 2:
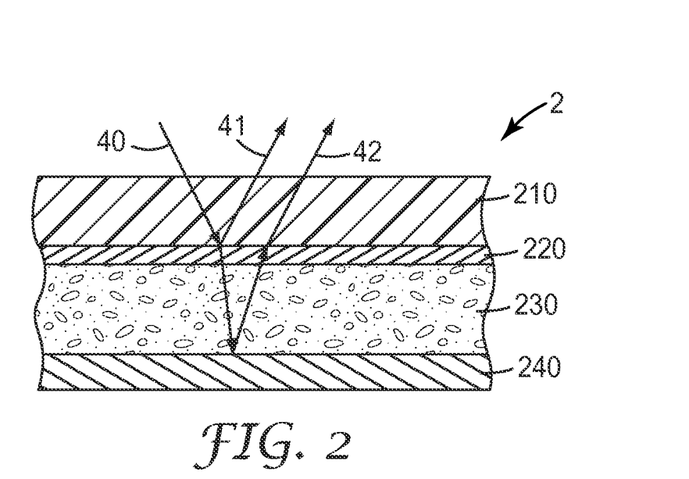
FIG. 2 is a side cross sectional view of a portion of an exemplary sensing element.
Figure 3:
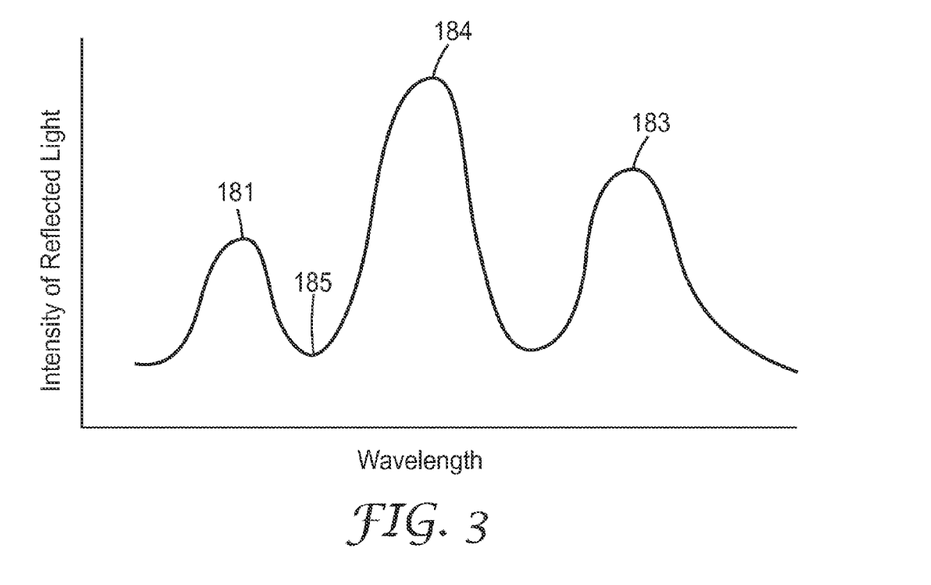
FIG. 3 is a generic representation of a reflectance spectrum exhibited by an exemplary sensing element.

Disclosed herein is sensing element 2, shown in various exemplary embodiments in FIGS. 1 and 2. Sensing element 2 is a multilayer structure containing at least an optically responsive layer 230 that is between a reflective layer 240 and a semireflective layer 220, the layers combining to comprise a so-called interference filter exhibiting a reflectance spectrum that may change in the presence of an analyte. Sensing element 2 exhibits a reflectance spectrum of the general type shown in generic representation in FIG. 3 and that comprises one or more peaks (e.g., 181, 183, and 184) and valleys (e.g., 185) at different wavelengths and that may change in the presence of an analyte or upon a change in the concentration of an analyte (this and all other references to concentration herein refer to the concentration of an analyte in an atmosphere to which the sensing element is exposed). For example, the presence of sufficient analyte may cause the peaks and valleys of FIG. 3 to be shifted to higher (longer) wavelengths. The reflectance spectrum exhibited by sensing element 2 may be manifested upon visual inspection as an appearance (e.g., a relatively dominant color, hue, or shade) that may change upon exposure to sufficient analyte. Thus, upon exposure to a sufficient concentration of analyte, sensing element 2 may change in appearance from a first (initial) appearance to a second appearance that is visually distinguishable from the first appearance.

Sensing element 2 may be optically interrogated by exposing sensing element 2 to incoming light rays 40 (as shown in FIGS. 1 and 2) and observing light reflected from sensing element 2. A dedicated (external) light source is not needed to provide light rays 40 (although one or more dedicated light sources may be so used if desired). Light rays 40 may originate from a single discrete light; or, ambient light (which may originate from several discrete light sources, from a combination of light from direct sources and from reflected light, from sunlight, etc.) may be used as the source of light rays 40.

In embodiments of the general type exemplified in FIG. 1, sensing element 2 comprises in order semireflective layer 220, optically responsive layer 230, reflective layer 240, and substrate 210. In interrogation of sensing element 2, light rays 40 impinge on semireflective layer 220. Some portion of light rays 40 may reflect from semireflective layer 220 as light rays 41. Another portion of light rays 40 may pass through semireflective layer 220 and pass through optically responsive layer 230 to encounter reflective layer 240. At least a portion of these light rays may reflect from reflective layer 240, to emerge from sensing element 2 as light rays 42. Light rays 41 and 42 may combine (e.g., by constructively and/or destructively interfering) to collectively provide a reflectance spectrum that may change in the presence of an analyte or upon a change in the concentration of an analyte.

In the exemplary design of FIG. 1, analyte may permeate through semireflective layer 220 to enter optically responsive layer 230. This may change the optical properties (e.g., the optical thickness) of at least a portion of layer 230 (e.g., a sublayer of layer 230, as disclosed in detail later herein) such that the reflectance spectrum of light reflected from sensing element 2 may change sufficiently to allow the presence of, and/or the concentration of, an analyte to be detected or monitored.

In embodiments incorporating the design shown in FIG. 1, semireflective layer 220 is analyte-permeable, which property can be provided as discussed later herein, and is in fluid communication with optically responsive layer 230, such that analyte can enter layer 230 through layer 220. In the design of FIG. 1, reflective layer 240 may or may not be analyte-permeable. In the design of FIG. 1, light may not need to pass through, or interact with, substrate 210, during optical interrogation of sensing element 2, so substrate 210 may not need any particular optical property (e.g., transparency).

Another exemplary sensing element 2 is shown in FIG. 2. In embodiments incorporating the design shown in FIG. 2, sensing element 2 comprises in order (optional) substrate 210, semireflective layer 220, optically responsive layer 230, and reflective layer 240. Light rays 40 impinge on and pass through substrate 210. Some portion of light rays 40 may reflect from semireflective layer 220 to emerge from sensing element 2 as light rays 41. Another portion of light rays 40 may pass through semireflective layer 220 and pass through optically responsive layer 230 to encounter reflective layer 240. At least a portion of these light rays may reflect from reflective layer 240, to emerge from sensing element 2 as light rays 42. Light rays 41 and 42 may combine to collectively provide a reflectance spectrum that may change in the presence of an analyte or upon a change in the concentration of an analyte.

In the exemplary design of FIG. 2, analyte may permeate through reflective layer 240 to enter optically responsive layer 230. This may change the optical properties (e.g., the optical thickness) of at least a portion of layer 230 (e.g., a sublayer of layer 230, as disclosed in detail later herein) such that the reflectance spectrum of light reflected from sensing element 2 may change sufficiently to allow the presence of, and/or the concentration of, an analyte to be detected or monitored. In embodiments incorporating the design shown in FIG. 2, reflective layer 240 is analyte-permeable, which property can be provided through methods discussed later herein, and is in fluid communication with optically responsive layer 230. In the design of FIG. 2, semireflective layer 220 may or may not be analyte-permeable. In the exemplary design of FIG. 2, light may pass through substrate 210, so substrate 210 should be optically clear at the wavelengths of interest.

Properties, methods of making, and so on, of optically responsive layer 230, and, if present, of substrate 210, semireflective layer 220, and/or reflective layer 240 will now be discussed in further detail. Such properties are understood to be applicable to the making of reflective (e.g., interference-based) sensing elements in general and in particular to either of the exemplary embodiments disclosed above with reference to FIGS. 1 and 2, except where specified to be applicable to a particular embodiment. Even though the same reference numbers are used to designate the above-referenced layers, those of ordinary skill in the art will readily appreciate that the layers so designated may have the same or different configurations and/or compositions.

Optically responsive layer 230 is defined as a layer comprising an optical thickness (physical thickness multiplied by refractive index) at least a portion of which can change in response to an analyte, such that a reflectance spectrum established by optically responsive layer 230 in combination with a suitable reflective layer 240 and semireflective layer 220 can sufficiently shift (e.g., such that a change in the visual appearance of sensing element 2 can be observed under the ordinary conditions in which sensing element 2 is to be used) upon exposure of sensing element 2 to a level of interest of an analyte of interest. Specifically, optically responsive layer 230, when provided between a suitable reflective layer 240 and semireflective layer 220, exhibits a reflectance spectrum that will shift by at least about 15 nm upon exposure to an atmosphere containing 1000 ppm of styrene, which is a suitable representative organic analyte of interest. This and all other references herein to a shift in reflectance spectrum are with reference to measurements performed according to the procedures outlined in the "Response of Samples to a Test Analyte" section of this disclosure. Optically responsive with respect to layer 230 further means that the total (physical) thickness of layer 230, counting all sublayers thereof, is generally on the order of, or near to, the wavelength of visible light (i.e., is from about 100 nm to about 2000 nm). In various specific embodiments, the total physical thickness of layer 230 may be from about 200 nm to about 1500 nm, from about 400 nm to about 1000 nm, or from about 500 nm to about 800 nm. (All thicknesses listed herein refer to physical thickness rather than optical thickness unless so specified).

Figure 4:
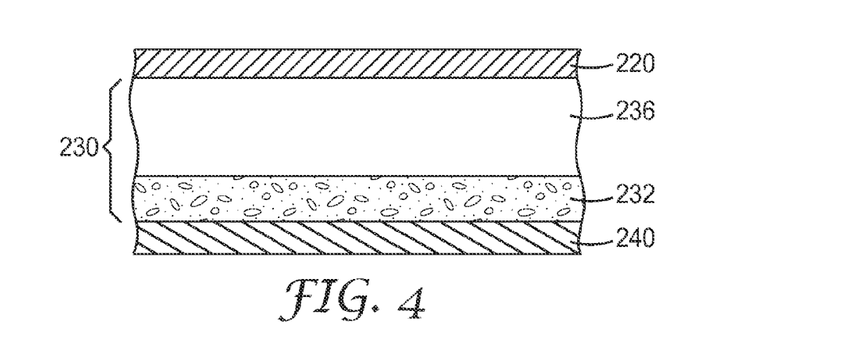
FIG. 4 is a side cross sectional view showing an optically responsive layer of a sensing element.

Optically responsive layer 230 may be comprised of at least two sublayers 232 and 236, as shown in FIG. 4. Sublayer 232 is a highly analyte-responsive sublayer as defined herein; sublayer 236 is a minimally analyte-responsive sublayer as defined herein. In various embodiments, the thickness of highly analyte-responsive sublayer 232 may be from about 100 nm to about 700 nm. In various embodiments, the thickness of minimally analyte-responsive sublayer 236 may be from about 700 nm to about 100 nm. In various embodiments, the combined thickness of sublayers 232 and 236 may be from about 200 nm to about 1500 nm. In specific embodiments, the combined thickness of sublayers 232 and 236 may be from about 400 nm to about 1000 nm, or from about 500 nm to about 800 nm. In various embodiments, the ratio of the thickness of sublayer 232 to that of sublayer 236 may range from about 1:8 to about 8:1. In specific embodiments, the ratio of the thickness of sublayer 232 to that of sublayer 236 may range from about 1:4 to about 4:1, or from about 1:2 to about 2:1.

In various embodiments, sublayers 232 and 236 may be in direct contact with each other and may be coterminous (e.g., in overlapping relation with each other and sharing identically shaped and sized borders). In further embodiments optically responsive layer 230 may be coterminous with reflective layer 240 and/or semireflective layer 220.

Sublayer 232 is highly responsive to an analyte of interest, which property is achieved by selection of the materials that comprise sublayer 232. In this context, highly responsive to an analyte means that sublayer 232 is sufficiently permeable to the analyte, and that the presence of analyte within sublayer 232 results in sufficient change in the optical thickness of sublayer 232 and hence in the optical thickness of layer 230, that an observable shift in the reflectance spectrum exhibited by sensing element 2 is produced. Specifically, the term highly analyte-responsive means that layer 232 is made of a material that, when consisting of a layer of thickness 400-800 nm between a suitable reflective layer and semireflective layer, exhibits a reflectance spectrum that will shift by at least about 15 nm upon exposure to an atmosphere containing 50 ppm of styrene. (As mentioned above, styrene may be used here and elsewhere herein as a useful representative organic analyte, i.e. as a convenient analyte for purposes of characterizing the responsiveness of materials useful in the inventions herein. The use of styrene in this manner in no way should be interpreted as limiting the use of the inventions disclosed herein to the monitoring of styrene). In various embodiments, highly analyte-responsive sublayer 232 is made of a material that, when consisting of a layer of thickness 400-800 nm between a suitable reflective layer and semireflective layer, exhibits a reflectance spectrum that, upon exposure to an atmosphere containing 50 ppm of styrene, will shift by at least about 25 nm, at least about 35, or at least about 45 nm.

Sublayer 236 is minimally responsive to the analyte of interest, which property is achieved by selection of the materials that comprise sublayer 236. In this context, minimally responsive to the analyte indicates either that sublayer 236 is not permeable to the analyte to a sufficient extent, and/or the presence of analyte within sublayer 236 does not result in a change in the optical thickness of sublayer 236 that is manifested as a change in the optical properties of layer 230 that results in an observable shift in the reflectance spectrum exhibited by sensing element 2. Specifically, the term minimally analyte-responsive means that sublayer 236 is made of a material that, when consisting of a layer of thickness 400-800 nm between a suitable reflective layer and semireflective layer, exhibits a reflectance spectrum that will shift by no more than about 10 nm upon exposure to an atmosphere containing 20 ppm of styrene. In various embodiments, minimally analyte-responsive sublayer 236 is made of a material that, when consisting of a layer of thickness 400-800 nm between a suitable reflective layer and semireflective layer, exhibits a reflectance spectrum that, upon exposure to an atmosphere containing 20 ppm of styrene, will shift by no more than about 5 nm, about 3 nm, or about 1 nm.

By using an optically responsive layer 230 that comprises a sublayer 232 that comprises a highly analyte-responsive material, and a sublayer 236 that comprises a minimally analyte-responsive material, the response of layer 230 (hence of sensing element 2) to a given level of analyte may be governed by the contributions of both sublayers. For example, a sensing element comprising an optically responsive layer 230 comprising a minimally analyte-responsive sublayer 236 may require a higher concentration of analyte to be present to cause a similar shift in reflectance spectrum, in comparison to a sensing element comprising an optically responsive layer 230 of similar thickness but not comprising a sublayer 236.

For example, in one embodiment sensing element 2 may comprise optically responsive layer 230 comprising highly analyte-responsive sublayer 232 and minimally responsive sublayer 236, configured so that (even though highly analyte-responsive sublayer 232 may be made of a material that, when consisting of a layer of thickness 400-800 nm between a suitable reflective layer and semireflective layer, exhibits a reflectance spectrum that will shift by, e.g., about 100 nm upon exposure to an atmosphere containing 200 ppm of styrene) sensing element 2 exhibits a reflectance spectrum shift of no more than about 40 nm upon exposure to an atmosphere containing 200 ppm of styrene. In further embodiments, such a sensing element may comprise sublayer 232 and sublayer 236 configured such that sensing element 2 exhibits a reflectance spectrum shift of no more than about 30 nm, or of no more than about 20 nm, upon exposure to an atmosphere containing 200 ppm of styrene.

Additionally, by using a minimally analyte-responsive sublayer 236 of selected thickness, this thickness being chosen to combine with the selected thickness of sublayer 232 to provide a selected total thickness of optically responsive layer 230, an initial reflectance spectrum (e.g., in the absence of analyte or in the presence of an undetectable level of analyte) of sensing element 2 can be established (for example, so as to impart sensing element 2 with a particular appearance (e.g., color) upon visual inspection). That is, a sensing element 2 employing sublayers 232 and 236 may be made with an initial appearance similar to that which would be exhibited by a sensing element 2 employing only a highly analyte-responsive material (e.g., not having a sublayer 236), and yet which responds to a different (e.g., higher) concentration of analyte than would a sensing element 2 employing only a highly analyte-responsive material.

Thus in summary, the use of optically responsive layer 230 comprising sublayers 232 and 236 may allow the selection of the concentration range of analyte to which sensing element 2 may respond to be selected, and also may allow an initial appearance of sensing element 2 to be selected. This combination may provide significant advantages.

The use of highly analyte-responsive sublayer 232 in combination with minimally analyte-responsive sublayer 236 may provide additional advantages at least in some embodiments. In particular, reflective sensors of the general type described herein have been known to those of skill in the art to potentially exhibit a phenomenon termed wraparound. In wraparound (upon exposure to a sufficiently high concentration of an analyte), the reflectance spectrum shifts so far that the sensing element changes appearance, back to an appearance similar to the initial appearance exhibited by the sensing element in the absence of analyte. (Further appearance changes may be possible upon exposure to still higher concentrations of analyte). The inventors have surprisingly found that the use of an optically responsive layer 230 comprising a highly analyte-responsive sublayer 232 in combination with a minimally analyte-responsive sublayer 236 can provide a sensing element 2 that is less susceptible to wraparound. In particular embodiments, the properties and thicknesses of sublayers 232 and 236 may be chosen such that sensing element 2 may not exhibit wraparound even in the presence of extremely high concentrations of analyte. For example, in various embodiments sensing element 2 may not exhibit wraparound even upon exposure to 200, 400, or even 1000 ppm of an organic analyte, e.g., styrene.

In various particular embodiments, such ability to not exhibit wraparound may correspond to the sensing element exhibiting a reflectance spectrum shift of less than about 100 nm, less than about 80 nm, or less than about 60 nm, upon exposure to 200 ppm of an organic analyte, e.g., styrene. In further particular embodiments, such ability to not exhibit wraparound may correspond to the sensing element exhibiting a reflectance spectrum shift of less than about 100 nm, less than about 80 nm, or less than about 60 nm, upon exposure to 400 ppm of an organic analyte, e.g., styrene. In additional particular embodiments, such ability to not exhibit wraparound may correspond to the sensing element exhibiting a reflectance spectrum shift of less than about 100 nm, less than about 80 nm, or less than about 60 nm, upon exposure to 1000 ppm of an organic analyte, e.g., styrene.

Highly analyte-responsive sublayer 232 can comprise any material that exhibits a sufficiently high response to analyte, e.g., in comparison to the particular minimally analyte-responsive sublayer 236 that it is used in combination with. Thus, sublayer 232 is sufficiently permeable to an analyte of interest, and comprises an optical thickness that can change sufficiently upon exposure to analyte of a chosen concentration to allow the desired functioning of sensing element 2 as described herein. Although not wishing to be bound or limited by any theory or mechanism, the optical thickness of sublayer 232 may change in response to an analyte, for example, via pore-filling (e.g., of a porous material at least partially comprising sublayer 232), which might serve to increase the optical thickness at least by increasing the refractive index. The optical thickness of sublayer 232 may also change in response to an analyte by swelling, which might serve to increase the optical thickness at least by increasing the physical thickness of the layer. Some materials may exhibit a mixture of both responses, may exhibit primarily one response at certain analyte concentrations and another response at other analyte concentrations, and so on.

In some embodiments, sublayer 232 comprises a porous material. In this context, "porous" means that the material comprises internal pores that are at least partially interconnected. Materials may be chosen, for example, with an average (mean) pore size (as characterized, for example, by sorption isotherm procedures) of less than about 100 nm. In various embodiments, materials may be chosen with an average pore size of less than 20 nm, less than about 10 nm, or less than about 2 nm. Sublayer 232 may be homogeneous or heterogeneous, and may, for example, be made from one or more inorganic components, one or more organic components, or a mixture of inorganic and organic components. Representative inorganic materials that may be used in sublayer 232 include metal oxides, metal nitrides, metal oxynitrides and other inorganic materials that can be formed into transparent (and if desired porous) layers of appropriate thickness for producing a suitable optical response. For example, sublayer 232 may comprise silicon oxides, silicon nitrides, silicon oxynitrides, aluminum oxides, titanium oxides, titanium nitride, titanium oxynitride, tin oxides, zirconium oxides, zeolites or combinations thereof.

Porous silica may be an especially desirable inorganic analyte-responsive layer material. Porous silicas may be prepared, for example, using a sol-gel processing route and made with or without an organic template. Exemplary organic templates include surfactants, e.g., anionic or nonionic surfactants such as alkyltrimethylammonium salts, poly(ethyleneoxide-co-propylene oxide) block copolymers and other surfactants or polymers. The sol-gel mixture may be converted to a silicate and the organic template may be removed to leave a network of pores within the silica. A variety of organic molecules may also be employed as organic templates. For example, sugars such as glucose and mannose may be used as organic templates to generate porous silicates. Organo-substituted siloxanes or organo-bis-siloxanes may be included in the sol-gel composition to render the micropores more hydrophobic and limit sorption of water vapor. Plasma chemical vapor deposition may also be employed to generate porous inorganic analyte-responsive materials. This methodology generally involves forming a plasma from gaseous precursors, depositing the plasma on a substrate to form an amorphous random covalent network layer, and then heating the amorphous covalent network layer to form a porous amorphous random covalent network layer. Such methods and materials are described in further detail in International (PCT) Published Patent Application No. U.S. 2008/078281, titled ORGANIC CHEMICAL SENSOR COMPRISING PLASMA-DEPOSITED MICROPOROUS LAYER, AND METHOD OF MAKING AND USING, which is incorporated by reference herein for this purpose.

In some embodiments, optically responsive layer 230 is comprised at least in part of porous organo-silicate materials, herein defined as compositions that are hybrids containing a covalently linked three dimensional silica network (—Si—O—Si—) with some organo-functional groups R, where R is a hydrocarbon or heteroatom substituted hydrocarbon group linked to the silica network by at least one Si—C bond. Such materials and methods of their making are described in further detail in U.S. Provisional Patent Application Ser. No. 61/140,131, titled AMORPHOUS MICROPOROUS ORGANOSILICATE COMPOSITIONS, which is incorporated by reference herein for this purpose.

In some embodiments, highly analyte-responsive layer 232 is made at least partially from components chosen from the family of materials comprising so-called "polymers of intrinsic microporosity" (hereafter called PIMs). Polymers in this family are described and characterized in, for example, "Polymers of Intrinsic Microporosity (PIMs): Robust, Solution-Processable, Organic Microporous Materials," Budd et al., *Chem. Commun.*, 2004, pp. 230-231; in "Polymers of Intrinsic Microporosity (PIMs)," McKeown et al., *Chem. Eur. J.*, 2005, 11, No. 9, 2610-2620; in U.S. Published Patent Application No. 2006/0246273 to McKeown et al.; and in International (PCT) Published Patent Application No. WO 2005/012397A2 to McKeown et al., all of which are incorporated by reference herein for this purpose.

PIMs can be formulated via the use of any combination of monomers that lead to a very rigid polymer within which there are sufficient structural features to induce a contorted structure. In various embodiments, PIMs can comprise organic macromolecules comprised of generally planar species connected by rigid linkers, said rigid linkers having a point of contortion such that two adjacent planar species connected by the linker are held in non-coplanar orientation. In further embodiments, such materials can comprise organic macromolecules comprised of first generally planar species connected by rigid linkers predominantly to a maximum of two other said first species, said rigid linkers having a point of contortion such that two adjacent first planar species connected by the linker are held in non-coplanar orientation. In various embodiments, such a point of contortion may comprise a spiro group, a bridged ring moiety or a sterically congested single covalent bond around which there is restricted rotation.

In a polymer with such a rigid and contorted structure, the polymer chains are unable to pack together efficiently, thus the polymer possesses intrinsic microporosity. Thus, PIMs have the advantage of possessing microporosity that is not significantly dependent on the thermal history of the material. PIMs thus may offer advantages in terms of being reproducibly manufacturable in large quantities, and in terms of not exhibiting properties that change upon aging, shelf life, etc.

In some embodiments, optically responsive layer 230 is comprised at least in part of porous, highly crosslinked polymeric materials, for example the hypercrosslinked styrenic resins known as "Styrosorbs" (as described for example in V. A. Davankov and P. Tsyurupa, Pure and Appl. Chem., vol. 61, pp. 1881-89 (1989) and in L. D. Belyakova, T. I. Schevchenko, V. A. Davankov and M. P. Tsyurupa, Adv. in Colloid and Interface Sci. vol. 25, pp. 249-66, (1986)), and including those materials available from Purolite (Bala Cynwyd, Pa.) under the trade designation Styrosorb.

For many applications, it may be advantageous that sublayer 232 be hydrophobic. In such embodiments, this may reduce the chance that water vapor (or liquid water) will cause a change in the response of sublayer 232 and interfere with the detection of an analyte, for example, the detection of organic solvent vapors. In some embodiments, highly analyte-responsive sublayer 232 is made of a material that, when provided as a layer of thickness 400-800 nm between a suitable reflective layer and a suitable semireflective layer, exhibits a reflectance spectrum that will shift by no more than 15 nm upon exposure to an atmosphere containing 90% humidity.

Further details and attributes of suitable materials useful for sublayer 232, and methods of making sublayer 232 from such materials, are described in e.g., U.S. Published Patent Application No. 2008/0063874, which is incorporated by reference herein for this purpose.

In various embodiments, sublayer 232 may comprise combinations (e.g., mixtures, blends, composite structures, and the like) of the above-listed materials, and/or multiple layers of such materials.

Minimally analyte-responsive sublayer 236 can be comprised of any material that first, exhibits sufficiently low (including nonexistent and/or nonmeasurable) optical response to an analyte (and to any other substance that might interfere with the sensing of the analyte of interest), in comparison to the particular highly analyte-responsive sublayer 232 that it is used in combination with; that second, is compatible with the processing methods used to produce sublayer 232 (as described later herein); and that third, is optically compatible with sublayer 232. By optically compatible is meant that sublayer 236 is comprised of a material or materials that are sufficiently transparent to light, and that comprise a refractive index that is sufficiently similar to that of sublayer 232, to permit the functioning of sensing element 2. That is, the difference in the refractive index of sublayers 232 and 236 should not be so large as to result in reflections emanating from the interface between sublayers 232 and 236 sufficient to interfere with the functioning of sensing element 2 (e.g., by unacceptably preventing a certain amount of light from reaching highly analyte-responsive sublayer 232, for example in a configuration in which light has to pass through sublayer 236 to reach sublayer 232). Optically compatible with respect to sublayer 236 further means that sublayer 236 does not contain any interfaces, particles, fillers, cavities, etc., that sufficiently reflect, absorb, and/or scatter light so as to unacceptably interfere with the reflectance spectrum of sensing element 2.

Sublayer 236 may be minimally-responsive to analyte due to sublayer 236 being relatively impermeable to the analyte of interest, such that insufficient analyte penetrates into sublayer 236 to cause a response. Thus, in various embodiments sublayer 236 may be comprised of materials with enhanced barrier properties. (In such case, sublayer 236 may preferably be positioned on the opposite side of highly analyte-responsive sublayer 232 from which analyte permeates into sensing element 2, so that analyte can reach sublayer 232). Sublayer 236 thus might be at least partially comprised of a semicrystalline polymeric material (e.g., with a high melting point ($T_m$)), and/or a glassy material (e.g., with a high glass transition temperature ($T_g$)), an inorganic network material (without interconnecting pores), and the like. In some embodiments, sublayer 236 may be at least somewhat permeable to the analyte, but may possess properties such that the presence of analyte (at least up to a certain level) within sublayer 236 does not cause an optical response (e.g., a change in optical thickness of sublayer 236). Thus, materials which have been suitably crosslinked so as to exhibit e.g. little tendency to swell in the presence of certain materials (e.g., water, organic vapors, etc.) may be chosen.

In some embodiments, sublayer 236 comprises a nonporous material. In other embodiments, sublayer 236 comprises a material which is porous, but in which such porosity does not prevent the material from being minimally analyte-responsive. For example, such material may comprise a very low level of porosity and/or may contain pores that are not interconnected (such that the ability of an analyte to permeate into the material is low), or may comprise pores of such large size that an analyte of interest does not condense in the pores until the sensing element is in the presence of a concentration of analyte that is higher than the concentration range of interest.

In various embodiments, sublayer 236 is comprised of a hydrophobic material or materials (which may minimize the chance of water interfering with the detection of certain analytes). In some embodiments, minimally analyte-responsive sublayer 236 is made of a material that, when consisting of a layer of thickness 400-800 nm between a suitable reflective layer and semireflective layer, exhibits a reflectance spectrum that will shift by no more than 15 nm upon exposure to an atmosphere containing 90% humidity.

Particularly in embodiments in which highly analyte-responsive sublayer 232 is deposited onto minimally analyte-responsive sublayer 236 via solution coating (as discussed later), it may be advantageous for the material of sublayer 236 to be resistant to being dissolved, degraded, or otherwise damaged by the solvent used to deposit sublayer 232. In the case that layer 232 comprises an aforementioned polymer of intrinsic microporosity (PIM), it may be useful for sublayer 236 to be resistant to such solvents as are commonly used to solubilize PIMs (e.g., chlorobenzene, chloroform, tetrahydropyran, tetrahydrofuran, and/or mixtures thereof).

In some embodiments, sublayer 236 comprises an uncrosslinked organic polymeric material. In such case, the polymeric material may be chosen to be resistant to absorbing, and/or swelling as a result of absorbing, an analyte or analytes of interest (e.g., organic vapors and the like). Exemplary materials that may be useful include poly(methacrylonitrile) and copolymers and blends thereof. Examples of sensing elements employing certain materials of this type are found in the discussion of samples 1-5. Other polymeric materials that may be suitable candidates (e.g., by virtue of their comprising a relatively high $T_m$ and/or $T_g$ and being relatively hydrophobic) may include for example poly(cyanomethyl acrylate), poly(3,5-dimethyladamantyl crotonate), poly(1-adamantyl acrylate), poly(adamantyl crotonate), poly(pentabromobenzyl acrylate), poly(pentachlorophenyl acrylate), poly(adamantyl methacrylate), poly(4-cyanophenyl methacrylate), poly(3,5-diadamantyl methacrylate), poly(3-tetracyclododecyl methacrylate), poly(2,6-xylenyl methacrylate), poly(methyl β-chloroacrylate), poly[4-(4-biphenylyl)styrene], poly[3-(4-biphenylyl)styrene], poly(2-carboxystyrene), poly(2,4-diisopropylstyrene), poly(2,5-diisopropylstyrene), poly[4-(1-hydroxy-1-methylethyl) styrene], poly[4-(1-hydroxy-1-methylpropyl)styrene], poly (2-hydroxymethylstyrene), poly(4-hydroxymethylstyrene), poly(4-iodostyrene),poly(α-methylstyrene), poly(perfluorostyrene), and poly(4-phenylstyrene).

In some embodiments, sublayer 236 comprises a crosslinked organic polymeric material. Such crosslinking may provide a material with enhanced resistance to absorbing, and/or swelling as result of absorbing, an analyte or analytes of interest, and thus may render a wide variety of materials useful for service in sublayer 236. For example, sublayer 236 may comprise a crosslinked polystyrene material. An example of a sensing element employing such materials is found in the discussion of sample 7. However, any suitable crosslinkable organic polymeric material, of any desired composition or structure, and optionally including additives and the like as are well known in the art, may be used.

In some embodiments, sublayer 236 comprises a crosslinked organic polymeric network achieved by the polymerization and/or reaction of multifunctional monomers, such as the well-known acrylate and methacrylate monomers. Mixtures of such monomers may for example be deposited (either as liquids, or via vapor-condensation methods for example as disclosed in U.S. Pat. No. 5,877,895) and reacted (e.g. radiation-cured) to form a crosslinked layer. Suitable monomers, oligomers, etc. that may be used for such purposes are disclosed for example in U.S. Pat. No. 7,449,146, incorporated by reference herein for this purpose. As mentioned, such layers should be prepared under such conditions so as to achieve properties (e.g., a high degree of crosslinking) that render them suitable to serve as sublayer 236. Other vapor coated organic polymeric materials may be used in sublayer 236, including for example the well-known coatings available from various sources under the trade designation Parylene. Whether crosslinked or uncrosslinked, it may be desirable for sublayer 236 to be hydrophobic, as mentioned previously.

Sublayer 236 may also comprise an inorganic material, e.g., that does not comprise porosity. As discussed above, the refractive index of the inorganic material should be sufficiently similar to that of sublayer 232 to permit the proper functioning of sensing element 2. For example, sublayer 236 may comprise silicon oxide (e.g., deposited by vapor coating). Such an inorganic material may comprise the entire thickness of sublayer 236. Or, sublayer 236 may comprise a barrier sublayer of inorganic material that is adjacent to sublayer 232, with a backing sublayer (e.g., of organic polymeric material) being behind the inorganic barrier sublayer and being present to provide the desired total thickness of sublayer 236. (An example of a sensing element employing such an approach is found in the discussion of sample 6). If the inorganic material is sufficiently impermeable to the analyte, the backing layer may be comprised of any suitable material (e.g., without particular regard to any need to be impermeable to the analyte) since in this configuration it may simply serve as a space filler and thus its barrier properties and/or responsiveness to the analyte may not be a factor.

In various embodiments, sublayer 236 may comprise combinations (e.g., mixtures, blends, composite structures, and the like) of the above-listed materials, and/or multiple layers of such materials.

Sensing element 2 may comprise reflective layer 240. In some embodiments, reflective layer 240 may be deposited (e.g., by various methods described herein) upon the surface of a previously formed optically responsive layer 230; or, reflective layer 240 may be deposited onto substrate 210 with other layers and/or sublayers of sensing element 2 then being deposited thereon.

Reflective layer 240 may comprise any suitable material that can provide sufficient reflectivity. Suitable materials for the reflective layer may include metals or semi-metals such as aluminum, chromium, gold, nickel, silicon, titanium, platinum, palladium, and silver. Other suitable materials that may be included in the reflective layer may include metal oxides. In some embodiments, the reflective layer may be at least about 90% reflective (i.e., at most about 10% transmissive), and in some embodiments, about 99% reflective (i.e., about 1% transmissive), at a wavelength of about 500 nm.

In some embodiments (e.g., incorporating the design of FIG. 2), reflective layer 240 may advantageously be permeable to an analyte of interest. This may be provided, for example, by forming reflective layer 240 of metal nanoparticles arranged in a morphology which approximates a stack of marbles and through which the analyte can permeate to reach and enter optically responsive layer 230.

A variety of metal nanoparticles may be employed. Representative metals include silver, nickel, gold, platinum and palladium and alloys containing any of the foregoing. Metals prone to oxidation when in nanoparticle form (e.g., aluminum) might be used but desirably would be avoided in favor of less air-sensitive metals. The metal nanoparticles may be monolithic throughout or may have a layered structure (e.g., a core-shell structure such as an Ag/Pd structure). The nanoparticles may, for example, have an average particle diameter of about 1 to about 100, about 3 to about 50 or about 5 to about 30 nm. The overall thickness of the metal nanoparticle layer may, for example, be less than about 500 nm or less than about 200 nm, and the minimum layer thickness may, for example, be at least about 5 nm, at least about 10 nm or at least about 20 nm. Although large diameter microparticles might be applied to form a monolayer, the nanoparticle layer typically will be several nanoparticles thick, e.g., at least 2 or more, 3 or more, 4 or more or 5 or more nanoparticles, and with up to 5, up to 10, up to 20 or up to 50 nanoparticles total thickness. The metal nanoparticle reflective layer may, for example, have a reflectance of at least about 40%, at least about 50% or at least about 60% at 500 nm. In various embodiments, the metal nanoparticle reflective layer may have a reflectance of at least about 80%, of at least about 90%, or of about 99%, at a wavelength of about 500 nm.

Solutions or suspensions of suitable metal nanoparticles are available from several suppliers, including Inkjet Silver Conductor ink AG-IJ-G-100-S1 (from Cabot Printable Electronics and Displays); SILVERJET™ DGH 50 and DGP 50 ink (from Advanced Nano Products); SVW001, SVW102, SVE001, SVE102, NP1001, NP1020, NP1021, NP1050 and NP1051 inks from Nippon Paint (America); METALON™ FS-066 and JS-011 inks from Novacentrix Corp. and NP Series nanoparticle paste from Harima Chemicals, Inc. The metal nanoparticles may be borne in a variety of carriers, including water, and organic solvents (e.g. methanol, heptane, decane, etc.). The metal nanoparticles may also be borne in a polymerizable monomeric binder but desirably such binder is removed from the applied coating (using e.g., solvent extraction or sintering) so as to provide a permeable nanoparticle layer.

Layer 240 may be formed by applying a dilute coating solution or suspension of metal nanoparticles to optically responsive layer 230 and allowing the solution or suspension to dry to form permeable reflective layer 240. The dilution level may, for example, be such as to provide a coating solution or suspension that will provide a suitably liquid- or vapor-permeable metal nanoparticle layer, for example solids levels less than 30 wt. %, less than 20 wt. %, less than 10 wt. %, less than 5% or less than 4%. By diluting an as-received commercial metal nanoparticle product with additional solvent and applying and drying the dilute solution or suspension, an appreciably thin, liquid- or vapor-permeable layer can be obtained. A variety of coating techniques can be employed to apply the metal nanoparticle solution or suspension, including swabbing, dip coating, roll coating, spin-coating, spray coating, die coating, ink jet coating, screen printing (e.g., rotary screen printing), gravure printing, flexographic printing and other techniques that will be familiar to persons having ordinary skill in the art. Accordingly, some silver nanoparticle suspensions available at low solids levels (such as 5 wt. % SVW001 silver from Nippon Paint or 10 wt. % SILVERJET DGH-50 or DGP-50 from Advanced Nano Products) might be usable in the as-received form without further dilution if spin-coated at an appropriately high speed and temperature onto a suitable substrate. The metal nanoparticle layer may be sintered after it has been applied (e.g., by heating at about 125 to about 250 degrees C. for about 10 minutes to about 1 hour) so long as the sintering does not cause a loss of adequate permeability. It will be understood that the resulting reflective layer may no longer contain readily-identifiable nanoparticles, but that it may be referred to as a nanoparticle reflective layer to identify the manner in which it has been made.

Further details and attributes of suitable analyte-permeable materials useful for reflective layer 240, in particular metal nanoparticle materials, are described in e.g., U.S. Published Patent Application No. 2008/0063874, which is incorporated by reference herein for this purpose.

Sensing element 2 may comprise semireflective layer 220. In various embodiments, semireflective layer 220 may be deposited (e.g., by various methods described herein) upon the surface of a previously formed optically responsive layer 230; or, semireflective layer 220 may be deposited onto substrate 210, with other layers and/or sublayers of sensing element 2 being deposited onto semireflective layer 220 thereafter.

Semireflective layer 220 may comprise a reflectivity that is similar to, or lower than, reflective layer 240. Semireflective layer 220 can comprise any suitable material that can provide appropriate semireflectivity (e.g., when at an appropriate thickness). Suitable materials may include metals or semimetals such as aluminum, chromium, gold, nickel, silicon, palladium, platinum, titanium and silver. Other suitable materials may include metal oxides.

In various embodiments, semireflective layer 220 may be about 30 to about 70% reflective, or from about 40 to about 60% reflective, at a wavelength of about 500 nm.

In some embodiments (e.g., of the type incorporating the design of FIG. 1), semireflective layer 220 may advantageously be permeable to an analyte of interest. Thus, in this case it may be preferable to provide semireflective layer 220 at an appropriate thickness in order to provide appropriate reflectivity while permitting an analyte to permeate through semireflective layer 220 to reach and enter optically responsive layer 230. In some cases, a thickness in the general range of 5-10 nm may be desired (e.g., if semireflective layer 220 is deposited by vapor deposition to form a metal layer). Specific desired thicknesses will depend on the material used to form the layer, the analyte to be detected, and may be configured as necessary.

Semireflective layer 220 and reflective layer 240 may be made from similar or the same materials (e.g., deposited at different thicknesses or coating weights, so as to impart the desired differences in reflectivity). Semireflective layer 220 and reflective layer 240 may be continuous or discontinuous, as long as the properties of reflectivity and permeability that are desired for a particular application are provided. Further details of suitable semireflective layers and reflective layers, their properties and methods of making, are described for example in U.S. Published Patent Application No. 2008/0063874, incorporated by reference herein for this purpose.

Substrate 210, if present, may be comprised of any suitable material (e.g., glass, plastic, etc.) capable of providing support for the sensing element. In embodiments in which light passes through substrate 210 in order for sensing element 2 to be interrogated, substrate 210 should be optically clear (i.e., should comprise sufficient transparency at the wavelengths of interest) and should not have other properties (e.g., fluorescence) that would unacceptably affect the optical signal. Suitable materials for substrate 210 may include for example the well known polyester family of polymers (e.g., poly(ethylene terephthalate) and poly(ethylene naphthalate)).

As mentioned, the total thickness of optically responsive layer 230 may be generally in the range of 400-800 nm and the thickness of sublayers 232 and 236 each may be in the range of 100-700 nm. It may not be practical to provide sublayer 232 and/or sublayer 236 as a freestanding film to be incorporated into sensing element 2 (e.g., by lamination), since freestanding films of such small thicknesses may be difficult to produce and/or handle. Thus, in various embodiments sublayers 232 and/or 236 may be sequentially deposited (e.g., onto an existing layer for example such as semireflective layer 220 atop substrate 210) such as by solution deposition, vapor deposition, and the like. Such methods might include for example spin coating, solution coating, extrusion coating, plasma deposition, plasma polymerization, and so on. Sublayer 236 may for example be deposited by solution coating followed by removal of solvent, optionally followed by a crosslinking treatment according to various known methods. Alternatively, sublayer 236 may be provided by deposition (e.g., by methods disclosed previously herein) of multifunctional monomers and/or oligomers that are then cured and crosslinked. If sublayer 236 comprises an aforementioned inorganic material, this may be provided by any of known deposition methods including those noted above. If desired, sublayers 232 and/or 236 may comprise multiple layers deposited by any of these various processes.

Reflective layer 240 and/or semireflective layer 220 may be provided by vapor coating methods including for example sputtering, evaporation, chemical vapor deposition, plasma deposition, and the like, or via coating or plating out of solution.

In an exemplary method of making a sensing element 2 of the general type shown in FIG. 2, optically clear substrate 210 is obtained (e.g. comprising polyester film and the like) and semireflective layer 220 is deposited thereupon. Minimally analyte-responsive sublayer 236 is then deposited atop semireflective layer 220. Highly analyte-responsive sublayer 232 is then deposited upon sublayer 236, in such manner as to not unacceptably remove, destroy or damage sublayer 236. Analyte-permeable reflective layer 240 is then deposited upon sublayer 232, via methods disclosed herein, so as to be in fluid communication with sublayer 232. Other layers, substrates, protective encapsulants, carriers, etc. may be added as long as the functioning of sensing element 2 is preserved.

Prior to use, a sensing element as disclosed herein may be maintained (e.g. packaged) in an environment substantially free of an analyte of interest. In such an environment, and/or prior to being exposed to an atmospheric concentration of analyte sufficient to cause a response, the sensing element may display a first appearance (e.g., color). Upon being exposed to an atmosphere containing a sufficiently high concentration of an analyte of interest, the reflectance spectrum exhibited by sensing element 2 may change (e.g., shift by a number of nanometers, typically to a longer wavelength) such that the sensing element undergoes a visually observable change from the first appearance to a second appearance that is different from the first appearance.

The optical response exhibited by the sensing element is typically observable in the visible light range and can be detected by the human eye as a change in appearance. Such a change in appearance may comprise e.g. a change from a first color to a second color, a change in the perceived brightness of the sensing element (e.g., while remaining generally in the same color range), a change from a relatively colorless appearance to a more colorful appearance, a change from a generally uniform appearance to a more nonuniform (e.g., variegated) appearance, and the like. While optical interrogation thus may in some embodiments be performed by visual inspection (e.g., by a person), in some embodiments other interrogation methods may be used, including for example an external interrogation device such as a spectrophotometer, photo-detector, charge coupled device, photodiode, digital camera, and the like. Use of such optoelectronic methods for interrogation of sensing element 2 is discussed in U.S. Provisional Patent Application Ser. No. 61/164,496, herein incorporated by reference for this purpose.

A sensing element as disclosed herein may be used to detect and/or monitor one or more analytes of interest. Such an analyte may comprise a vapor or gas that may be present in an environment (often, an air atmosphere) that is desired to be monitored. In some embodiments, the analyte is an organic vapor (e.g., a volatile organic compound). In specific embodiments, the analyte is a high boiling organic compound, defined herein as an organic compound having a boiling point of 100° C. or greater. Representative organic analytes may include substituted or unsubstituted carbon compounds including alkanes, cycloalkanes, aromatic compounds, alcohols, aldehydes, ethers, esters, ketones, halocarbons, amines, organic acids, cyanates, thiols, nitrates, and nitriles, for example n-octane, cyclohexane, methyl ethyl ketone, acetone, ethyl acetate, carbon disulfide, carbon tetrachloride, benzene, toluene, styrene, xylenes, chloroform, tetrahydrofuran, methanol, ethanol, isopropyl alcohol, n-butyl alcohol, t-butyl alcohol, 2-ethoxyethanol, acetic acid, 2-aminopyridine, ethylene glycol monomethyl ether, toluene-2,4-diisocyanate, nitromethane, acetonitrile, and the like. (Of these, styrene may serve as a representative organic analyte useful in characterizing the response of sensing element 2, optically responsive layer 230, highly analyte-responsive sublayer 232, and/or minimally analyte-responsive sublayer 236, as discussed herein. Others may also serve).

In some cases sensing element 2 may be used to detect water (e.g., as a humidity sensor). In other embodiments, sensing element 2 may be designed (e.g., through selection of hydrophobic materials for sublayers 232 and/or 236) to have minimal response to the presence of water.

Sensing elements as described herein may be used in various applications. In some embodiments, sensing element 2 may be used in connection with a respiratory protection device (e.g., a respirator, such as might contain a filter element, sorbent media, etc., for removal of certain substances from an atmosphere) to provide a so-called end of service life indicator (ESLI) that can monitor an atmosphere comprising an air stream that has passed at least partially through a filter element, sorbent media, etc. present in the respiratory protection device, and that may indicate for example that the filter element, sorbent media, etc. may be exhausting its capacity to remove the analyte from the air stream. A single sensing element 2 may be used alone, or an array comprising multiple sensing elements 2 may be employed. Use of sensing element 2 and arrays of sensing element 2 in ESLI applications is discussed in further detail in copending U.S. Provisional Patent Application Ser. No. 61/180,492, titled MULTI-LAYER COLORIMETRIC SENSOR ARRAYS, filed evendate herewith, which is herein incorporated by reference.

Sensing element 2 may be used (again, alone or in an array) in personal monitor and/or area monitor applications, such as those of the general type discussed in U.S. Provisional Patent Application Ser. No. 61/148,228, herein incorporated by reference for this purpose.

EXAMPLES

All reagents and materials used in these examples were obtained from Sigma-Aldrich, St. Louis, Mo., unless otherwise noted.

Preparation of TFTN-PIM 1:

In a 2.0 L three-neck round bottomed flask, 33.4357 g of 3,3,3',3'-tetramethyl-1,1'-spirobisindane-5,5',6,6'-tetrol (tetrol) and 19.8016 g of tetrafluoroterephthalonitrile (TFTN) were dissolved in 900 mL of anhydrous N,N-dimethyl formamide (DMF). The solution was stirred with a mechanical stirrer, and nitrogen was bubbled through the solution for one hour. To this solution was added 81.4491 g of potassium carbonate (EMD Chemicals, Gibbstown, N.J.). The flask was placed in an oil bath at 68° C. The mixture was stirred at this elevated temperature under a nitrogen atmosphere for 65 hours. The polymerization mixture was poured into 9.0 L of water. The precipitate formed was isolated by vacuum filtration and washed with 600 mL of MeOH (VWR, West Chester, Pa.). The isolated material was spread out in a pan and allowed to air dry overnight. The solid was placed in a jar and dried under vacuum at 68° C. for 4 hours. The resulting yellow powder was dissolved in 450 mL of THF (EMD). This solution was poured slowly into 9.0 L of methanol. The precipitate formed was isolated by vacuum filtration. The isolated material was spread out in a pan and allowed to air dry overnight. The solid was placed in a jar and dried under vacuum at 68° C. for 4 hours. The precipitation in methanol was performed one more time. The resulting dried, bright yellow polymer weighed 42.80 g. Analysis of the polymer by GPC using light scattering detection showed the material to have a $M_n$ of approximately 30,900.

Preparation of TFTN-PIM 2:

In a 2.0 L three-neck round bottomed flask, 33.4365 g of tetrol and 19.8011 g of TFTN were dissolved in 900 ml of anhydrous DMF. The solution was stirred with a mechanical stirrer, and nitrogen was bubbled through the solution for one hour. To this solution was added 81.4480 g of potassium carbonate. The flask was placed in an oil bath at 68° C. The mixture was stirred at this elevated temperature under a nitrogen atmosphere for 67.5 hours. The polymerization mixture was poured into 9.0 L of water. The precipitate formed was isolated by vacuum filtration and washed with 600 mL of MeOH. The isolated material was spread out in a pan and allowed to air dry overnight. The solid was placed in a jar and dried under vacuum at 68° C. for 4 hours. The resulting yellow powder was dissolved in 450 mL of THF. This solution was poured slowly into 9.0 L of methanol. The precipitate formed was isolated by vacuum filtration. The isolated material was spread out in a pan and allowed to air dry overnight. The solid was placed in a jar and dried under vacuum at 68° C. for 4 hours. The precipitation in methanol was performed one more time. The resulting dried, bright yellow polymer weighed 43.22 g. Analysis of the polymer by GPC using light scattering detection showed the material to have a $M_n$ of approximately 35,800.

Preparation of Sample 1:

A metalized polyethylene terephthalate (PET) substrate was prepared by evaporatively depositing a 10 nm-thick Ni metal layer onto Melinex ST505 (Dupont Teijin) clear PET. A 4% by weight solution of TFTN-PIM 1 in chlorobenzene (Alfa Aesar, Ward Hill, Mass.) was prepared and deposited onto the Ni-coated PET by slot die coating, to a thickness of approximately 600 nm. A silver nanoparticle layer was deposited by slot die coating onto the TFTN-PIM layer using 100 g of stock nanosilver suspension (DGP-40LT-15C from Advanced Nanoproducts, Korea, 40% by weight silver) diluted with 150 g of 1-methoxy-2-propanol (Dow Chemical, Midland, Mich.). After deposition, the overall sensor construction was heated at 150° C. for 1 hour to sinter the silver nanoparticles.

Preparation of Sample 2:

A Ni-coated PET substrate was prepared as described in Preparation of Sample 1. A 6% by weight solution of poly (methacrylonitrile) (PMAN) (Scientific Polymer Products, Inc., Ontario, N.Y., $M_w$ of approximately 20,000) in nitromethane (EMD) was prepared, and the solution was coated onto the Ni-PET substrate by spin coating at 2100 rpm for 2 minutes using a WS-400B-8NPP-Lite Single Wafer spin processor manufactured by Laurell Technologies, Corp., North Wales, Pa. A 2% by weight solution of TFTN-PIM 2 in chlorobenzene was prepared and coated on top of the PMAN layer by spin coating at 1500 rpm. A 0.5 g quantity of the commercially available silver nanoparticle suspension described in the Preparation of Sample 1 was diluted with 1 mL of methanol. This silver nanoparticle suspension was coated on top of the TFTN-PIM layer by spin coating at 1000 rpm. After deposition, the overall sensor construction was heated at 150° C. for 1 hour to sinter the silver nanoparticles. The overall thickness of the PMAN/TFTN-PIM was approximately 600 nm with the TFTN-PIM layer being approximately 100 nm thick.

Preparation of Sample 3:

A Ni-coated PET substrate was prepared as described in Preparation of Sample 1. A 6% by weight solution of PMAN in cyclohexanone (EMD) was prepared, and the solution was coated onto the Ni-PET substrate by spin coating at 1100 rpm. A 3% by weight solution of TFTN-PIM 2 in chlorobenzene was prepared and coated on top of the PMAN layer by spin coating at 1500 rpm. A 0.5 g quantity of the commercially available silver nanoparticle suspension described in the Preparation of Sample 1 was diluted with 1 mL of methanol. This silver nanoparticle suspension was coated on top of the TFTN-PIM layer by spin coating at 1000 rpm. After deposition, the overall sensor construction was heated at 150° C. for 1 hour to sinter the silver nanoparticles. The overall thickness of the PMAN/TFTN-PIM was approximately 600 nm with the TFTN-PIM layer being approximately 200 nm thick.

Preparation of Sample 4:

A Ni-coated PET substrate was prepared as described in Preparation of Sample 1. A 6% by weight solution of PMAN in cyclohexanone was prepared, and the solution was coated onto the Ni-PET substrate by spin coating at 1500 rpm. A 4% by weight solution of TFTN-PIM 2 in chlorobenzene was prepared and coated on top of the PMAN layer by spin coating at 3000 rpm. A 0.5 g quantity of the commercially available silver nanoparticle suspension described in the Preparation of Sample 1 was diluted with 1 mL of methanol. This silver nanoparticle suspension was coated on top of the TFTN-PIM layer by spin coating at 1000 rpm. After deposition, the overall sensor construction was heated at 150° C. for 1 hour to sinter the silver nanoparticles. The overall thickness of the PMAN/TFTN-PIM was approximately 600 nm with the TFTN-PIM layer being approximately 250 nm thick.

Preparation of Sample 5:

A Ni-coated PET substrate was prepared as described in Preparation of Sample 1. A 6% by weight solution of PMAN in cyclohexanone was prepared, and the solution was coated onto the Ni-PET substrate by coating at 1900 rpm. A 4% by weight solution of TFTN-PIM 2 in chlorobenzene was prepared and spin coated on top of the PMAN layer by spin coating at 2000 rpm. A 0.5 g quantity of the commercially available silver nanoparticle suspension described in the Preparation of Sample 1 was diluted with 1 mL of methanol. This silver nanoparticle suspension was coated on top of the TFTN-PIM layer by spin coating at 1000 rpm. After deposition, the overall sensor construction was heated at 150° C. for 1 hour to sinter the silver nanoparticles. The overall thickness of the PMAN/TFTN-PIM was approximately 600 nm with the TFTN-PIM layer being approximately 300 nm thick.

Preparation of Sample 6:

A Ni-coated PET substrate was prepared as described in Preparation of Sample 1. A 10% by weight solution of poly (vinylidene chloride-co-acrylonitrile-co-methyl methacrylate) (Sigma-Aldrich; $M_w$ approximately 13,000, $M_n$ approximately 84,000) (PVnCl) in cyclohexanone was prepared, and the solution was coated onto the Ni-PET substrate by spin coating at 1500 rpm. A 500 angstrom layer of $SiO_x$ was evaporatively deposited on top of the PVnCl layer. A 4% by weight solution of TFTN-PIM 2 in chlorobenzene was prepared and coated on top of the $SiO_x$ layer by spin coating at 3000 rpm. A 0.5 g quantity of the commercially available silver nanoparticle suspension described in the Preparation of Sample 1 was diluted with 1 mL of methanol. This silver nanoparticle suspension was coated on top of the TFTN-PIM layer by spin coating at 1000 rpm. After deposition, the overall sensor construction was heated at 150° C. for 1 hour to sinter the silver nanoparticles. The overall thickness of the PVnCl/$SiO_x$/TFTN-PIM was approximately 600 nm with the TFTN-PIM layer being approximately 250 nm thick.

Preparation of Sample 7:

A Ni-coated PET substrate was prepared as described in Preparation of Sample 1. A 7% by weight solution of polystyrene (Sigma-Aldrich, $M_w$ approximately 280,000) (PSt) in toluene was prepared, and the solution was coated onto the Ni-PET substrate by spin coating at 2500 rpm. The sample was placed under a germicidal lamp and irradiated for 18 hours. A 4% by weight solution of TFTN-PIM 2 in chlorobenzene was prepared and coated on top of the crosslinked PSt layer by spin coating at 3000 rpm. A 0.5 g quantity of the commercially available silver nanoparticle suspension described in the Preparation of Sample 1 was diluted with 1 mL of methanol. This silver nanoparticle suspension was coated on top of the TFTN-PIM layer by spin coating at 1000 rpm. After deposition, the overall sensor construction was heated at 150° C. for 1 hour to sinter the silver nanoparticles. The overall thickness of the PSt/TFTN-PIM was approximately 600 nm with the TFTN-PIM layer being approximately 250 nm thick.

Response of Samples to a Test Analyte

A simple flow-through custom built delivery system was used to deliver known concentrations of a test analyte (styrene) to the sensing element for measurement. Teflon tubing was used throughout the delivery system. Liquid styrene (Alfa Aesar, 99%, Prod #A18481) was delivered onto a heated platen at a specified flow rate by way of a Harvard Apparatus syringe pump. The platen was located in a 500-mL round bottom flask through which 20 L/min dry air (relative humidity less than about 5%) flow was maintained. The concentration of styrene in the gaseous stream was calibrated by use of an infrared spectrometer (available under the designation Miran Sapphire from ThermoElectron of Waltham, Mass.). The gaseous styrene stream was introduced into a sample chamber (held at room temperature) containing the sensing element sample.

Figure 5:
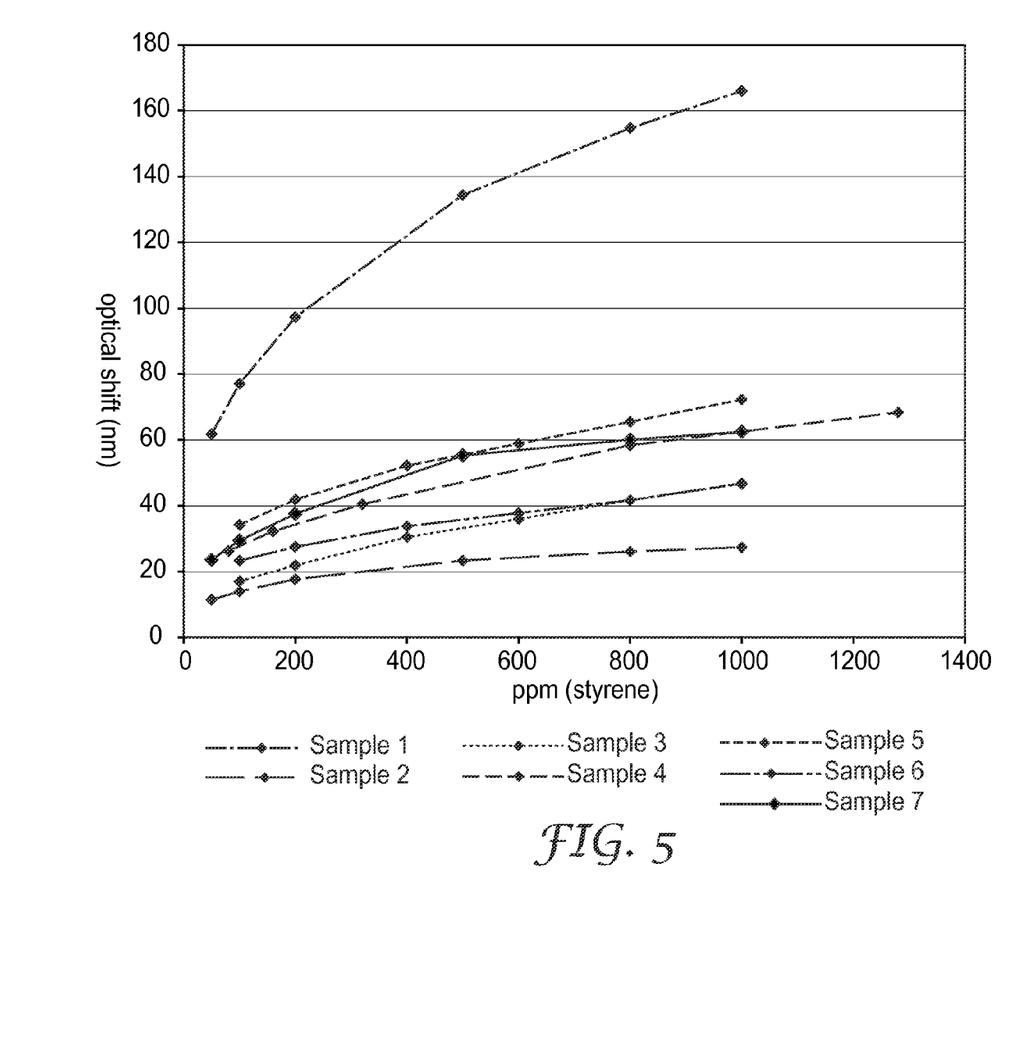
FIG. 5 is a plot of experimentally obtained data showing the observed wavelength shift upon exposure to various concentrations of a test analyte, for various sensing elements.

In this manner various individual sensing element samples were sequentially exposed to gaseous streams containing styrene in a concentration range of from 50 to 1300 parts per million. The length of exposure of each sample to a specific concentration of styrene was typically around 50-60 minutes. During the exposure, the sample was optically interrogated via a spectrometer (available from Ocean Optics under the trade designation USB 2000), used with an LS-1 tungsten-halogen lamp as light source, and with a fiber optic reflection probe, and the wavelength spectrum (e.g., similar to that generically shown in FIG. 3) was recorded. For each exposure level, the wavelength shift (measured as the shift in nanometers of a peak (typically a peak with a maxima at approximately 570 nm wavelength)) was recorded (relative to the initial peak location in the absence of analyte). The results of this testing for samples 1-7 are plotted in FIG. 5.

Individual samples 1-7 all exhibited a similar initial appearance (green in color) when viewed from a similar viewing angle, prior to their exposure to the test analyte. Generally with these samples, a wavelength shift (as measured above) of approximately 25 nm was associated with a visually observable change of the appearance of the sensing element from green to red. Thus, sample 1 might be expected to change from green to red when exposed to an atmosphere containing around 20 ppm styrene, sample 5, around 50 ppm, sample 4, around 80 ppm, sample 3, about 300 ppm, and sample 2, about 800 ppm.

Generally with exemplary sensing elements of this type comprising a total thickness (of optically responsive layer 230) of from about 400 nm to about 800 nm, the inventors have found a wavelength shift of around 80 nm to be associated with wraparound (e.g., the sensing element changing from a red color back to a green color similar to that exhibited initially by the sample in the absence of the analyte). Thus, sample 1 (in which the optically responsive layer was comprised only of a highly analyte-responsive (PIM) layer of approximately 600 nm thickness, with no minimally analyte-responsive layer being present) might be expected to exhibit wraparound upon exposure to an atmosphere containing around 100 ppm styrene. Notably, none of samples 2-7, which all contained a PIMS layer of no more than about 300 nm in thickness, and each of which contained a minimally analyte-responsive layer of such thickness as to make the total thickness of the optically responsive layer approximately 600 nm, exhibited a wavelength shift of 80 nm (which might be expected to result in wraparound), even upon exposure to relatively high levels of styrene. For instance, even sample 4, which was exposed to 1300 ppm of styrene, did not reach the 80 nm threshold.

The tests and test results described above are intended solely to be illustrative, rather than predictive, and variations in the testing procedure can be expected to yield different results. All quantitative values in the Examples section are understood to be approximate in view of the commonly known tolerances involved in the procedures used. The foregoing detailed description and examples have been given for clarity of understanding only. No unnecessary limitations are to be understood therefrom.

It will be apparent to those skilled in the art that the specific exemplary structures, features, details, configurations, etc., that are disclosed herein can be modified and/or combined in numerous embodiments. All such variations and combinations are contemplated by the inventor as being within the bounds of the conceived invention. Thus, the scope of the present invention should not be limited to the specific illustrative structures described herein, but rather by the structures described by the language of the claims, and the equivalents of those structures. To the extent that there is a conflict or discrepancy between this specification and the disclosure in any document incorporated by reference herein, this specification will control.

What is claimed is:

1. A optically interrogatable sensing element for sensing an organic vapor analyte, comprising:
   an optically responsive layer between a reflective layer and a semi-reflective layer,
   wherein the optically responsive layer comprises at least a first, highly analyte-responsive sublayer and a second, minimally analyte-responsive sublayer;
   wherein the second, minimally analyte-responsive sublayer is optically compatible with the first, highly analyte-responsive sublayer, wherein the second, minimally analyte-responsive sublayer and the first, highly analyte-responsive sublayer are in overlapping relation with each other and exhibit identically shaped and sized borders, and wherein the ratio of the thickness of the first, highly analyte-responsive sublayer to that of the second, minimally analyte-responsive sublayer is from about 1:5 to about 1:1;
   and wherein the sensing element does not exhibit wraparound upon exposure to an atmosphere containing 1000 ppm of an organic vapor analyte.

2. The sensing element of claim 1, wherein the highly analyte-responsive sublayer comprises a polymer of intrinsic microporosity.

3. The sensing element of claim 1, wherein the optically responsive layer comprises a total thickness of from about 400 nm to about 1000 nm.

4. The sensing element of claim 1 wherein the highly analyte-responsive sublayer comprises a thickness of less than about 500 nm and the minimally analyte-responsive sublayer comprises a thickness of greater than about 200 nm.

5. The sensing element of claim 1 wherein the highly analyte-responsive sublayer comprises a thickness of less than about 300 nm and the minimally analyte-responsive sublayer comprises a thickness of greater than about 300 nm.

6. The sensing element of claim 1 wherein the minimally analyte-responsive sublayer is impermeable to the analyte.

7. The sensing element of claim 1 wherein the minimally analyte-responsive sublayer is comprised of a hydrophobic material and the highly analyte-responsive sublayer is comprised of a hydrophobic material.

8. The sensing element of claim 1 wherein the minimally analyte-responsive sublayer comprises a crosslinked polymer network material.

9. The sensing element of claim 1 wherein the minimally analyte-responsive sublayer comprises at least a layer of inorganic nonporous material.

10. The sensing element of claim 9 wherein the layer of inorganic nonporous material comprises the entirety of the minimally analyte-responsive sublayer.

11. The sensing element of claim 9 wherein the minimally analyte-responsive sublayer comprises at least an inorganic nonporous analyte-impermeable layer that is adjacent the highly analyte-responsive sublayer, and an organic polymeric layer that is separated from the highly analyte-responsive layer by the inorganic nonporous sublayer.

12. The sensing element of claim 1 wherein the reflective layer is permeable to the analyte.

13. The sensing element of claim 12 wherein the reflective layer is a nanoporous layer comprising sintered nanoparticles.

14. The sensing element of claim 1 wherein the semireflective layer is permeable to the analyte.

15. The sensing element of claim 1 wherein the sensing element comprises a reflectance spectrum shift of less than about 40 nm upon exposure to an atmosphere containing 200 ppm of styrene.

16. The sensing element of claim 15 wherein the sensing element comprises a reflectance spectrum shift of less than about 25 nm upon exposure to an atmosphere containing 200 ppm of styrene.

17. The sensing element of claim 1 wherein the sensing element comprises a reflectance spectrum shift of less than about 80 nm upon exposure to an atmosphere containing about 1000 ppm of styrene.

18. The sensing element of claim 1 wherein the minimally analyte-responsive sublayer comprises a material chosen from the group consisting of poly(methacrylonitrile) and copolymers and blends thereof.

19. A method of making a sensing element for sensing an organic vapor analyte, comprising:
    forming a semireflective layer on an optically clear substrate;
    forming a sublayer of minimally analyte-responsive material atop the semireflective layer;
    forming a sublayer of highly analyte-responsive material atop the sublayer of minimally analyte-responsive material;
    and,
    forming an analyte-permeable reflective layer atop the sublayer of highly analyte-responsive material;
    wherein the sublayer of minimally analyte-responsive material is optically compatible with, the sublayer of highly analyte-responsive material, wherein the second, minimally analyte-responsive sublayer and the first, highly analyte-responsive sublayers are in overlapping relation with each other and exhibit identically shaped and sized borders, and wherein the ratio of the thickness of the first, highly analyte-responsive sublayer to that of the second, minimally analyte-responsive sublayer is from about 1:5 to about 1:1;
    and wherein the sensing element does not exhibit wrap-around upon exposure to an atmosphere containing 1000 ppm of an organic vapor analyte.

20. The method of claim 19 wherein the forming of the sublayer of minimally analyte-responsive material comprises depositing a solution on the semireflective layer and removing solvent from the solution to form a dried sublayer of minimally analyte-responsive material.

21. The method of claim 20 further comprising crosslinking the material of the dried sublayer of minimally analyte-responsive material.

22. The method of claim 19 wherein the forming of the sublayer of minimally analyte-responsive material comprises depositing, by vapor-condensation, multifunctional monomers and/or oligomers on the semireflective layer, and reacting the monomers and/or oligomers to form a crosslinked network of minimally analyte-responsive material.

23. The method of claim 19 wherein the forming of the sublayer of highly analyte-responsive material comprises depositing a solution on the sublayer of minimally analyte-responsive material and removing solvent from the solution to form a dried sublayer of highly analyte-responsive material.

24. The method of claim 23 wherein the minimally analyte-responsive material is not soluble in the solution used to form the sublayer of highly analyte-responsive material.

25. The method of claim 19 wherein the forming of the sublayer of minimally analyte-responsive material comprises depositing a layer of nonporous inorganic material.

\* \* \* \* \*

UNITED STATES PATENT AND TRADEMARK OFFICE
CERTIFICATE OF CORRECTION

| | |
|---|---|
| PATENT NO. | : 8,871,148 B2 |
| APPLICATION NO. | : 13/320925 |
| DATED | : October 28, 2014 |
| INVENTOR(S) | : Michael Wendland |

Page 1 of 1

It is certified that error appears in the above-identified patent and that said Letters Patent is hereby corrected as shown below:

In the Specification

Column 9
Line 9, Delete "styrenic" and insert -- styrene --, therefor.

Column 16
Line 10, Delete "61/180,492," and insert -- 61/180,492, Docket No. 65359US002, --, therefor.

Column 16
Lines 11-12, Delete "evendate herewith," and insert -- May 22, 2009, --, therefor.

In the Claims

Column 21, Claim 11
Lines 3-4, Delete "adjacent the highly analyte-responseive" and insert -- adjacent to the highly analyte-responseive --, therefor.

Column 22, Claim 19
Line 2, Delete "with," and insert -- with --, therefor.

Signed and Sealed this
Eighth Day of September, 2015

Michelle K. Lee
*Director of the United States Patent and Trademark Office*